United States Patent
Bayer et al.

(10) Patent No.: US 10,307,541 B2
(45) Date of Patent: Jun. 4, 2019

(54) DRIVE MECHANISM OF A DRUG DELIVERY DEVICE

(71) Applicant: Sanofi, Paris (FR)

(72) Inventors: Stefan Bayer, Würselen (DE); Daniel Berning, Baesweiler (DE); Philippe Blank, Düsseldorf (DE); Wolfgang Pelzer, Kreuzau (DE); Björn Wilden, Simmerath (DE)

(73) Assignee: Sanofi, Paris (FR)

( * ) Notice: Subject to any disclaimer, the term of this patent is extended or adjusted under 35 U.S.C. 154(b) by 118 days.

(21) Appl. No.: 14/783,514

(22) PCT Filed: Apr. 8, 2014

(86) PCT No.: PCT/EP2014/056977
§ 371 (c)(1),
(2) Date: Oct. 9, 2015

(87) PCT Pub. No.: WO2014/166899
PCT Pub. Date: Oct. 16, 2014

(65) Prior Publication Data
US 2016/0030678 A1 Feb. 4, 2016

(30) Foreign Application Priority Data

Apr. 10, 2013 (EP) .................................... 13163077

(51) Int. Cl.
*A61M 5/315* (2006.01)
*A61M 5/20* (2006.01)
*A61M 5/31* (2006.01)
(52) U.S. Cl.
CPC .......... *A61M 5/31541* (2013.01); *A61M 5/20* (2013.01); *A61M 5/31551* (2013.01);
(Continued)

(58) Field of Classification Search
CPC .......... A61M 5/31541; A61M 5/31551; A61M 5/31553; A61M 5/31583; A61M 5/31528;
(Continued)

(56) References Cited

U.S. PATENT DOCUMENTS

2008/0234633 A1* 9/2008 Nielsen .................. A61M 5/24
604/208
2008/0306445 A1 12/2008 Burren et al.
(Continued)

FOREIGN PATENT DOCUMENTS

WO WO 2004/078239 9/2004
WO WO 2010/139645 12/2010

OTHER PUBLICATIONS

Rote Liste, "50. Hypophysen-, Hypothalamushormone, andere regulatorische Peptide u. ihre Hemmstoffe," Chapter 50, ed. 2008, 20 pages.
(Continued)

*Primary Examiner* — Kami A Bosworth
*Assistant Examiner* — Alexandra Lalonde
(74) *Attorney, Agent, or Firm* — Fish & Richardson P.C.

(57) ABSTRACT

A drive mechanism of a drug delivery device for dispensing of a dose of a medicament includes a housing extending in an axial direction, and a piston rod to operably engage with a piston of a cartridge to displace the piston in an axial distal direction. The drive mechanism further includes a last dose sleeve rotatably supported in the housing and being selectively engageable with a dose setting mechanism for setting of a dose, and a last dose member threadedly engaged to the housing, rotatably locked to the last dose sleeve and axially displaceable relative to the last dose sleeve.

24 Claims, 14 Drawing Sheets

(52) U.S. Cl.
CPC .... *A61M 5/31553* (2013.01); *A61M 5/31583* (2013.01); *A61M 5/3157* (2013.01); *A61M 2005/3126* (2013.01); *A61M 2005/3154* (2013.01); *A61M 2205/581* (2013.01); *A61M 2205/582* (2013.01)

(58) Field of Classification Search
CPC ................ A61M 5/31533; A61M 5/20; A61M 5/31568; A61M 5/3158; A61M 5/31585; A61M 2005/3154
See application file for complete search history.

(56) References Cited

U.S. PATENT DOCUMENTS

| | | | |
|---|---|---|---|
| 2009/0137964 A1* | 5/2009 | Enggaard | A61M 5/178 604/207 |
| 2009/0198193 A1* | 8/2009 | Veasey | A61M 5/24 604/207 |
| 2011/0054412 A1 | 3/2011 | Eich et al. | |

OTHER PUBLICATIONS

International Preliminary Report on Patentability in International Application No. PCT/EP2014/056977, dated Oct. 13, 2015, 7 pages.
International Search Report and Written Opinion in International Application No. PCT/EP2014/056977, dated Jul. 24, 2014, 12 pages.

* cited by examiner

A-A

B-B

C-C

D-D

E-E

F-F

G-G

DRIVE MECHANISM OF A DRUG DELIVERY DEVICE

CROSS REFERENCE TO RELATED APPLICATIONS

This application is a National Stage application under 35 U.S.C. § 371 of International Application No. PCT/EP2014/056977, having an International Filing Date of Apr. 8, 2014, which claims the benefit of European Application No. 13163077.4 filed Apr. 10, 2013. This disclosure of the prior applications are considered part of (and are incorporated by reference in) the disclosure of this application.

The present disclosure relates to a drive mechanism for a drug delivery device and to a respective drug delivery device. In some aspects, the disclosure relates to an injection device such like a pen-type injector inter alia comprising a single and/or a last-dose limiting mechanism and further comprising a comparatively large dose indicating display.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, which is adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

With such multi-dose drug delivery devices at least a last dose limiting mechanism is required to inhibit setting of a dose exceeding the amount of medicament left in the cartridge. This is to avoid a potentially dangerous situation for the user believing that a set dose is entirely injected. There already exist some drug delivery devices with end-of-content mechanisms or last dose mechanisms.

Drug delivery devices such like pen type injectors also provide a dose indicating mechanism which is operable to display the size of a set dose to a user. Typically, the housing of such drug delivery devices comprises a dose indicating window in which a number representing the size of the dose shows up.

Especially with elderly patients or users suffering impaired vision, reading of such dose indicating numbers is sometimes difficult. With devices adapted for injection of e.g. insulin, typical dose sizes may vary between 0 and 120 I.U. (International Units) of insulin. Due to the rather compact design and limited geometrical dimensions of typical drug delivery devices the size of such dose indicating numbers is fairly small. For visually impaired persons correct reading of comparatively tiny numbers may therefore be rather difficult. However, since such drug delivery devices are intended for self-medication treatment, it is of importance, that the user is able to correctly determine the size of dose actually set.

SUMMARY

Certain aspects of the present invention avoid disadvantages of known drug delivery devices and provide drive mechanisms of drug delivery devices allowing for an intuitive operation, both for setting and for dispensing of a dose. Some aspects provide dose indicating mechanisms which are easy and unequivocal to read even for persons suffering impaired vision.

Some aspects serve to provide drive mechanisms of a drug delivery devices for setting and dispensing of a dose of a medicament and further featuring single and/or last dose limiting mechanisms.

Moreover, the drive mechanism can be rather compact to limit the overall size of the drug delivery device.

Some aspects further provide drug delivery devices comprising such a drive mechanism and comprising a cartridge sealed with a piston and being operably engaged with a piston rod of such drive mechanism. The drug delivery device can be rather easy and intuitive to handle.

In a first aspect a drive mechanism of a drug delivery device is provided for dispensing of a dose of a medicament. The drive mechanism comprises an elongated housing extending in an axial direction. The housing is of substantially tubular or cylindrical shape that allows gripping and operating of the drive mechanism and of the drug delivery device by only one hand of a user.

The drive mechanism further comprise a piston rod to operably engage with a piston of a cartridge containing the medicament to be dispensed by the drive mechanism. The cartridge comprises a piston at its proximal end, which, by means of a displacement in axial distal direction serves to expel an amount of the medicament from the cartridge. The piston typically seals the cartridge in axial proximal direction.

The piston rod of the drive mechanism serves to displace the piston of the cartridge in axial distal direction for expelling a predefined amount of the medicament from the cartridge. Hence, the piston rod is operable to apply distally-directed thrust or pressure to the piston of the cartridge for displacing the same in distal direction for a predetermined distance that corresponds to a respective amount or dose of the medicament to be dispensed.

Moreover, drive mechanism comprises a last dose sleeve rotatably supported in the housing and being selectively engageable with a dose setting mechanism for setting of a dose. The dose setting mechanism typically comprises at least a drive sleeve which is operably engageable with the last dose sleeve during a dose setting procedure and which is typically disengageable from the last dose sleeve during dose dispensing.

The drive sleeve is alternately engageable either with the piston rod or with the last dose sleeve during dose dispensing and dose setting, respectively. The dose setting mechanism may also include other functional components, such like a dose indicating mechanism, by way of which the size of a dose actually set can be visually displayed to a user, e.g. via a dose indicating window of the housing. The last dose sleeve is rotatably supported in the housing of the drive mechanism and may be operable to exclusively rotate in a dose incrementing way.

While the dose setting mechanism may return into an initial, hence into a zero dose configuration during dose dispensing, the last dose sleeve is typically decoupled from the dose setting mechanism during a dose injection procedure. Instead, the last dose sleeve is particularly intended and adapted to consecutively rotate in a dose incrementing direction during consecutive dose setting procedures. In this way, the configuration or the number of turns of the last dose sleeve is directly indicative of the total number or total size of doses already set and dispensed by the drive mechanism.

Moreover, the drive mechanism also comprises a last dose member or last dose limiting member threadedly engaged to the housing and being rotatably locked to the last dose sleeve. The last dose member is further axially displaceable relative to the last dose sleeve. In particular, the last dose member is splined to the last dose sleeve. In this way, a rotation of the last dose sleeve relative to the housing leads to an axial displacement of the last dose member relative to the housing and relative to the last dose sleeve.

Typically, a rotation of the last dose sleeve relative to the housing leads to an axial displacement of the last dose member on the last dose sleeve. The last dose member is displaceable along the housing and/or along the last dose sleeve until it engages with a stop by way of which a further displacement of the last dose member relative to the last dose sleeve and/or relative to the housing can be effectively impeded or blocked.

In such a stop or blocking configuration, the dose setting mechanism is effectively disabled to be operated any further in dose incrementing direction. The mutual arrangement of last dose sleeve, housing and last dose member is configured such, that the axial position of the last dose member relative to the last dose sleeve or relative to the housing directly reflects the axial position of the piston rod. In situations, where the amount of medicament left in the cartridge is less than the maximum size of a single dose to be set by the dose setting mechanism, the arrangement of last dose member, last dose sleeve and housing is operable to prevent setting of a dose exceeding the amount of medicament left in the cartridge.

In this way the last dose sleeve and the last dose member effectively serve to limit an incrementing dose setting that would otherwise exceed the residual amount of medicament left in the cartridge.

The last dose sleeve, the last dose member and the housing therefore provide a last dose limiting mechanism, by way of which setting of a dose exceeding the residual amount of medicament left in the cartridge can be effectively prevented.

By way of threadedly engaging the last dose member with the housing a rather robust and reliable support for the last dose limiting member can be provided. Moreover, when providing also a stop e.g. at the end of a threaded portion of the housing, a rather reliable and precise stop configuration for the dose limiting member can be attained.

Moreover, by having the last dose limiting member threadedly arranged with the housing, an initial assembly of the components of the drive mechanism may be facilitated. For instance, the last dose member may be mounted and arranged to a distal end of the last dose sleeve, which may then be inserted into the housing in a well-defined way, thereby automatically establishing and supporting a threaded engagement of the last dose member with the housing.

Typically, the last dose member comprises a radially outwardly extending outer thread to engage with a correspondingly shaped radially inwardly extending thread provided on an inside facing portion of e.g. a tubular housing portion. Moreover, the last dose sleeve may comprise a longitudinally or axially extending fixing structure allowing for an axial displacement of the last dose member relative to the last dose sleeve.

Apart from this rotational interlocking structure of last dose sleeve and last dose member, the last dose member may comprise a substantially flat or smooth shaped radially inwardly directed support surface to slide or to glide along a correspondingly shaped, substantially smooth or flat outer surface of the last dose sleeve.

In this way, last dose member and last dose sleeve comprise substantially smooth or flat shaped contact surfaces, which allow for a smooth gliding of the last dose member relative to the last dose sleeve, e.g. during dose setting. Moreover, mutually corresponding rather smooth or flat shaped contact surfaces of last dose sleeve and last dose member serve to counteract any tilt or cant of the last dose member relative to the last dose sleeve.

According to a further embodiment, the last dose member is arc-shaped and comprises an outer thread to engage with an inner thread of the housing. Typically, the last dose member extends about 180° around the substantially tubular shaped last dose sleeve. Such a semicircular shape of the last dose member allows to arrange the last dose member onto the last dose sleeve by a radially directed assembly process.

In this context it is also conceivable, that the last dose member also slightly exceeds an outer circumference of 180° so as to provide a kind of snap-type preassembly of the last dose member on the outer circumference of the last dose sleeve. However, there is generally no need, that the last dose member comprises a semicircular or half nut shape. It is generally sufficient, when the last dose member for instance extends about 30° or 60° in circumferential direction on the outer circumference of the last dose sleeve.

According to another embodiment, the last dose member and the last dose sleeve comprise an axially extending groove to receive a correspondingly shaped radially extending protrusion. In another embodiment it is the last dose member that comprises a radially inwardly extending protrusion to engage with a correspondingly shaped recess or groove on the outer circumference of the last dose sleeve, which extends in axial direction.

However, in alternative embodiments it is also conceivable, that it is the last dose sleeve that comprises a radially outwardly extending protrusion to mate with a correspondingly shaped radially outwardly extending recess provided on an inner contact surface of the last dose member. Moreover, it is conceivable, that last dose member and the last dose sleeve comprise two pairs of mutually corresponding protrusions and grooves. In this way, a tilt or cant of the last dose member relative to the last dose sleeve can be effectively prevented.

According to another embodiment, the last dose member comprises at least one radially extending stop face at a circumferential end section thereof to engage with a correspondingly shaped radially extending stop at an inside facing portion of the housing. Such radially extending mutually corresponding stops of the last dose member and the housing provide a well-defined blocking configuration when a last dose stop configuration of the drive mechanism has been reached.

Since the last dose sleeve is operable to rotate in circumferential direction relative to the housing, the mutually corresponding radially outwardly or radially inwardly extending stops of housing and dose member are operable to immediately and to precisely block any further rotational displacement of last dose sleeve and housing relative to each other.

Naturally, the stop faces of the last dose member and the housing not only extend in radial but also in axial direction to provide a respective stop surface. It is due to the axial displacement of the last dose member during a last turn of the last dose sleeve that mutually corresponding stop faces of last dose member and housing may get in a circumferentially overlapping configuration. As soon as the last dose configuration has been reached, the respective stop faces of the last dose member and the housing mutually abut in circumferential direction, thereby inhibiting any further rotational displacement of the stop faces and the respective components related thereto.

In a further embodiment, the last dose sleeve also comprises a radially outwardly extending flange portion at an axial end to support the last dose member in an initial assembly configuration. The radially outwardly extending flange portion of the last dose sleeve thereby provides an assembly support for the last dose member.

During assembly of the drive mechanism, the last dose member may be mounted on the last dose sleeve in a well-defined way in axial abutment with the last dose sleeve's flange portion.

The flange portion of the last dose sleeve may be provided at a proximal or at a distal end thereof. When provided at a proximal end of the last dose sleeve, the threaded engagement of the last dose member and the housing is such that the last dose member advances in distal direction during consecutive dose setting procedures.

When the flange portion of the last dose sleeve is however provided on a distal end thereof, the threaded engagement will serve to displace the last dose member in proximal direction during setting of a dose. Accordingly, the housing will provide the radially inwardly extending stop face in a region axially offset from the initial position of the last dose member and hence axially offset from the radially outwardly extending flange portion of the last dose sleeve.

In another embodiment, the last dose sleeve is axially constrained between a drive wheel and an insert axially fixed to the housing. Thus, the radially outwardly extending flange portion of the last dose sleeve may serve to axially engage with a housing portion or with any further functional components of the drive mechanism. Moreover, it is generally conceivable, that the last dose sleeve is axially fixed relative to the housing. Since it is constrained between the drive wheel and an insert of the housing it may also serve to axially fix neighbouring components, such like the drive wheel and/or the insert.

In this way, the last dose sleeve not only provides a last dose limiting function but may also serve as an axial spacer or distance member in order to constrain other components of the drive mechanism in the housing.

According to a further embodiment, the drive wheel is threadedly engaged with the piston rod being rotatably locked to the housing. The drive wheel, which is axially constrained by the last dose sleeve, is operable to induce a distally directed motion to the piston rod. The piston rod may be splined with the housing and may comprise at least one longitudinally or axially extending slot or notch to engage with a correspondingly shaped radially inwardly extending protrusion of the housing.

In this way, the piston rod may be rotatably locked to the housing. Since the piston rod is provided with an outer thread to engage with an inner thread of the axially constrained drive wheel, a rotation of the drive wheel therefore leads to a dose dispensing, hence distally directed displacement of the piston rod relative to the housing and/or relative to the drive wheel.

In another embodiment, it is also conceivable that the piston rod is threadedly engaged with the housing. In particular, the housing may comprise a radially extending web featuring a threaded through opening to mate with the outer thread of the piston rod. In this embodiment, the drive wheel may be rotatably locked to the piston in order to transfer a rotational displacement and a respective torque to the piston.

In another embodiment and independent on whether the drive wheel is splined or threadedly engaged with the piston rod, the drive mechanism comprises at least one axially extending clutch member extending through the hollow shaped last dose sleeve. Said clutch member, typically in form of a distal clutch member is axially displaceable relative to the last dose sleeve for selectively engaging a dose setting member with the last dose sleeve exclusively during dose setting.

By means of the at least one clutch member, the drive mechanism can be reversibly and selectively switched between a dose setting mode and a dose dispensing mode. By axially displacing the clutch member relative to the last dose sleeve, the dose setting member of the dose setting mechanism may be disengaged from the last dose sleeve during dose injection while it may be engaged by means of the clutch with the last dose sleeve during dose setting.

In still another embodiment, the clutch member is displaceable between a proximal stop position and a distal stop position. In the proximal stop position the clutch member is typically rotatably engaged with the last dose sleeve while it is simultaneously disengaged from the piston rod or from the drive wheel. However, in the distal stop position, the clutch member is rotatably engaged with the drive wheel, in particular for transferring a torque to the drive wheel for displacing the piston rod in distal direction.

In said distal stop position the clutch member is further disengaged from the last dose sleeve for not modifying the configuration thereof, in particular for not modifying the axial position of the last dose member on the last dose sleeve during dose dispensing. By means of the selective and alternate engagement of the clutch member with the last dose sleeve and the drive wheel, the last dose sleeve and hence the last dose member are only displaceable during consecutive dose setting procedures.

The relative displacement of the last dose member may accumulate during each consecutive dose setting displacement, thereby reflecting the position of the piston rod relative to the housing and/or relative to the cartridge after a subsequent dose dispensing procedure has been completed.

In a further embodiment, the clutch member comprises radially outwardly extending teeth at a distal end to selectively engage with correspondingly shaped radially inwardly extending teeth of the last dose sleeve. The last dose sleeve comprises a conically shaped toothed rim at a distal end to engage with a correspondingly shaped conical toothed outer rim of the distal clutch member.

Displacing the clutch member in distal direction relative to the axially fixed last dose sleeve serves to decouple the clutch member from the last dose sleeve. A reverse displacement of the clutch member relative to the last dose sleeve, e.g. at the end of a dispensing procedure may serve to re-engage the mutually corresponding toothed rims or toothed structures of clutch member and last dose sleeve. Since the toothed rim of the last dose sleeve provides a radially tapered structure as seen in proximal direction the toothed profile of the last dose sleeve may also effectively serve as a proximal stop for the clutch member.

According to another embodiment, the clutch member also comprises a crown wheel at its distal end face to engage with a correspondingly shaped crown wheel or crown wheel portion provided on a proximal end face of the drive wheel. In this way, mutually correspondingly shaped distal and proximal end faces of the distal clutch member and the drive wheel, provide a torque transmitting coupling of the clutch member and the drive wheel. Implementation of mutually corresponding crown wheels or crown wheel portions allows to reduce the overall radial dimensions of the clutch member and the drive wheel. Moreover, said crown wheel base connection allows to reduce the overall radial dimension of the drive mechanism and its housing.

Moreover, and according to another embodiment, the at least one clutch member is axially displaceable in distal direction against the action of a spring by means of a dose dispensing button which is located at a proximal end of the housing. The spring may be located elsewhere in the drive mechanism. The clutch member extending through the last dose sleeve is a distal clutch member interconnected with at least one further clutch member, e.g. with a main clutch member and/or with a proximal clutch member.

Various clutch members, proximal clutch member, main clutch member and distal clutch member may be all rotatably and axially coupled with each other so as to transfer a rotational as well as axial movement between the various clutch members, in particular in both dimensions and directions, hence in a dose incrementing as well as in a dose decrementing direction and as well as in distal and proximal direction.

Typically, the force or torque transmission provided by the various clutch members is bi-directional. Hence, a distal and/or proximal displacement as well as a dose incrementing or dose decrementing rotation of one of said clutch members equally transfers to the at least one further clutch member; and vice versa.

The spring serves to bias the at least one clutch member in its proximal stop configuration, in which the clutch member is rotatably engaged with the last dose sleeve. Hence, the spring serves to keep the drive mechanism in a dose setting mode. Displacement of a dose dispensing button, e.g. in distal direction may be transferred to the at least one clutch member for reversibly switching the drug delivery device into a dispensing mode against the action of the spring.

The spring may be integrated into at least one of the clutch members and may also serve to return the clutch members and hence the drive mechanism into a dose setting configuration when the distally directed dispensing force exerted to the dose dispensing button drops below a predefined activation threshold, e.g. at the end of a dispensing procedure or when a dose dispensing is prematurely interrupted.

According to another aspect, a drug delivery device for dispensing of a dose of a medicament comprises a drive mechanism as described above and a cartridge at least partially filled with the medicament to be dispensed by the drug delivery device. The cartridge is arranged in the housing of the drive mechanism or in a cartridge holder of the drug delivery device which is fixed to the housing either releasably or non-releasably, e.g. in case of a disposable drug delivery device. Consequently, the drug delivery device comprises a cartridge holder to receive and to accommodate a cartridge filled with the medicament.

In case of a disposable drug delivery device the cartridge is not to be replaced when empty but the entire device is intended to be discarded. With a reusable device, the drive mechanism can be reset and an empty cartridge can be generally replaced by a new one.

Apart from that, the drug delivery device and the drive mechanism may comprise further functional components, such like an injection button, by way of which a user may trigger and control the drug delivery device and its drive mechanism for dispensing of a dose of the medicament.

In the present context, the distal direction points in the direction of the dispensing and of the device, where a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

Generally, by means of the spring element operably engaged with the drive member, a semi-automated drug delivery device can be provided. During a dose setting procedure the spring element can be strained or tensioned to such a degree, that a dose dispensing action of the drug delivery device can be exclusively driven by the relaxing action of the biased spring element. Hence, dose dispensing is completely governed by the action of a spring element previously tensioned and strained in a dose setting procedure.

The drive mechanism particularly serves to displace a piston rod in axial direction for the purpose of dispensing of a dose of a medicament. In addition, the drive mechanism typically comprises at least one component which also forms part of and has a function in one of the following mechanisms: a dose setting mechanism, a last dose limiting mechanism and a dose indicating mechanism. As will be apparent from the embodiments described herein various components of e.g. the drive mechanism also belong to at least one of the dose setting mechanism, the last dose limiting mechanism and/or to the dose indicating mechanism; and vice versa. Hence, some aspects as described herein equally refer to and define a drive mechanism, a dose setting mechanism, a last dose limiting mechanism and/or a dose indicating mechanism of a drug delivery device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2,
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, an embodiment will be described by making reference to the drawings, in which.

DETAILED DESCRIPTION

Figure 1:
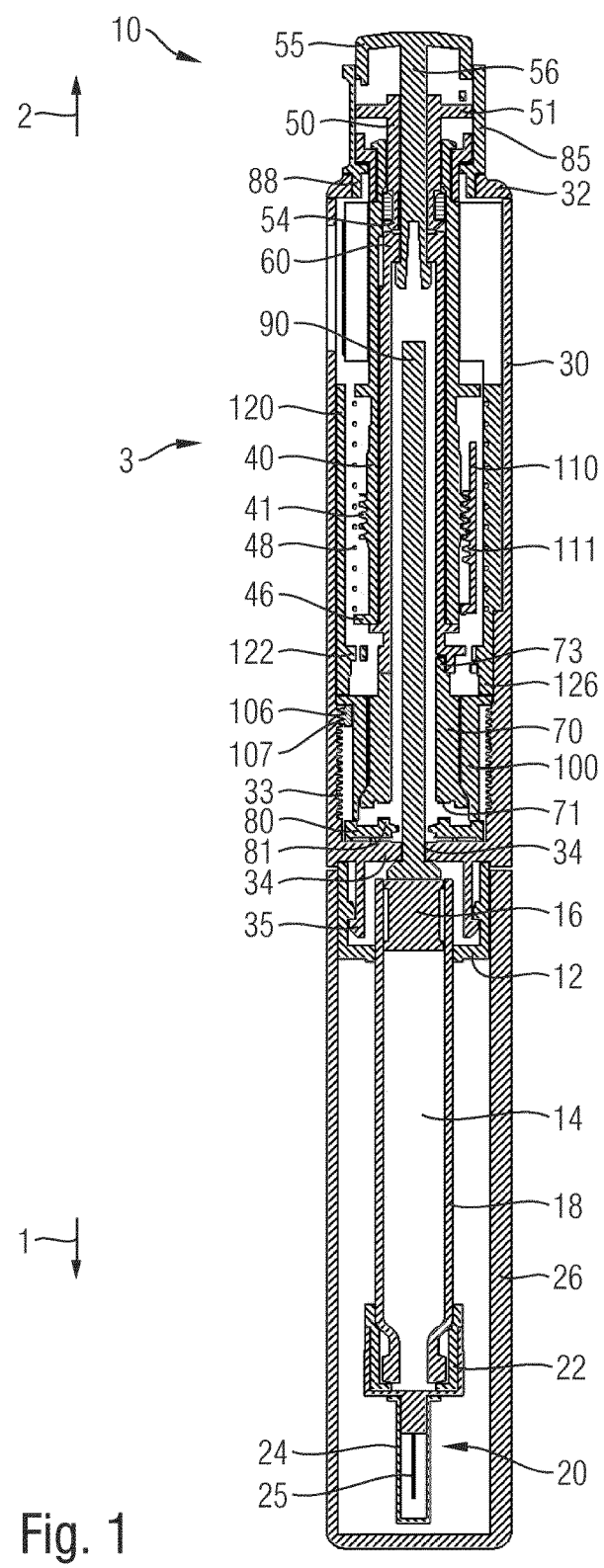
FIG. 1 schematically illustrates a drug delivery device in longitudinal cross-section.
Figure 2:
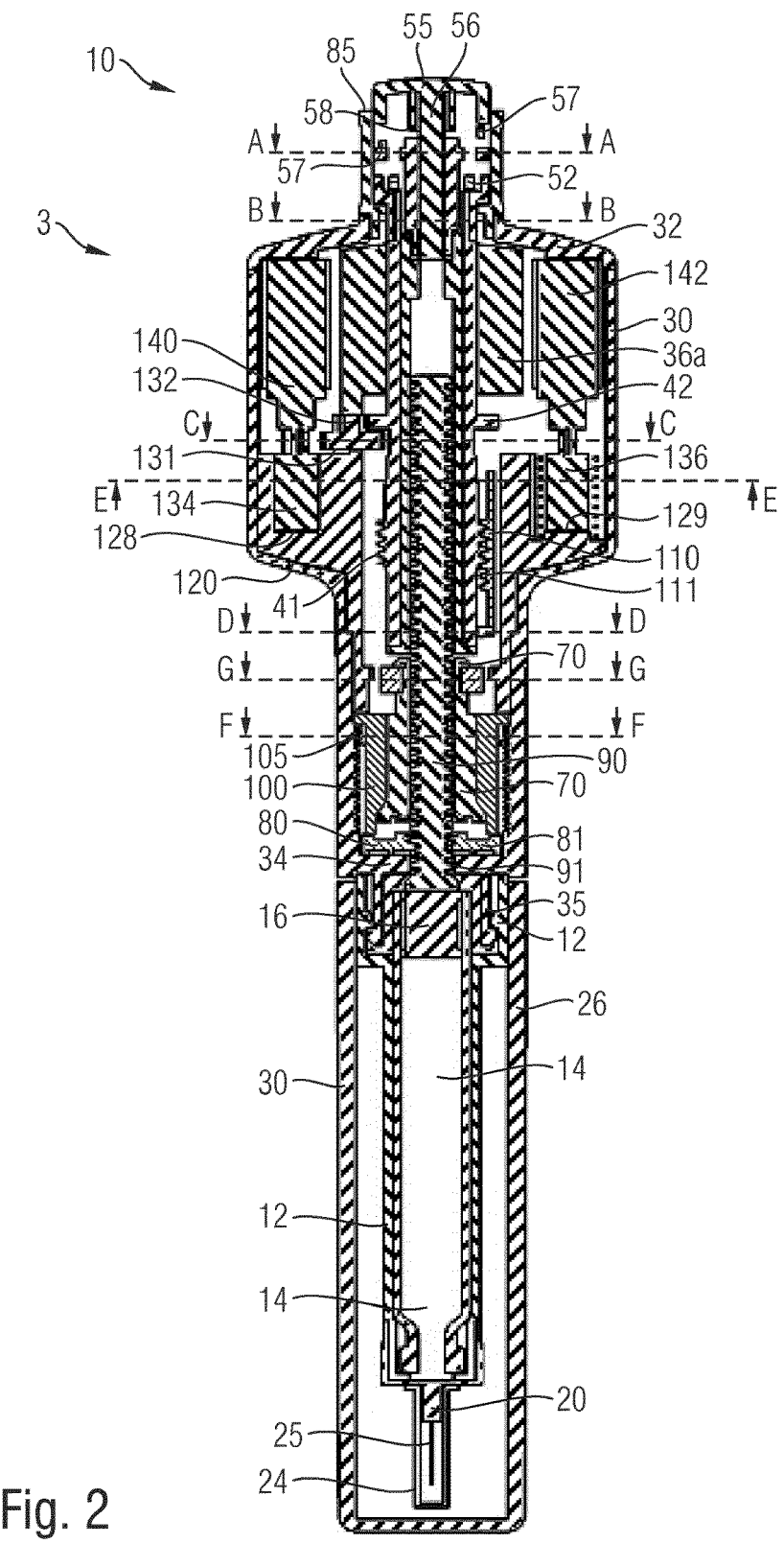
FIG. 2 shows another longitudinal cross-section of the drug delivery device rotated about 90° around its longitudinal axis.
Figure 10:
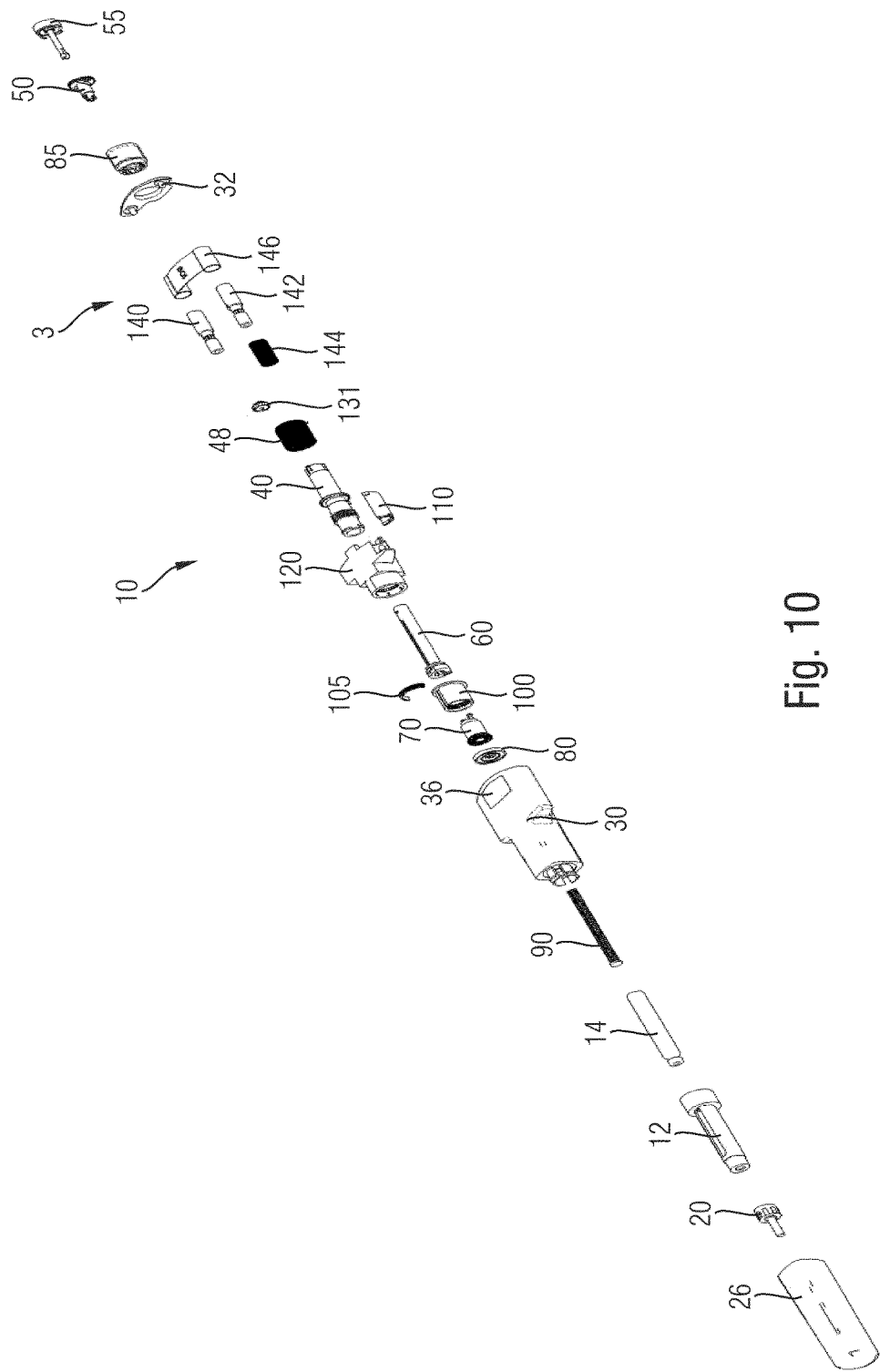
FIG. 10 shows an exploded view of the drug delivery device in perspective illustration.
Figure 11:
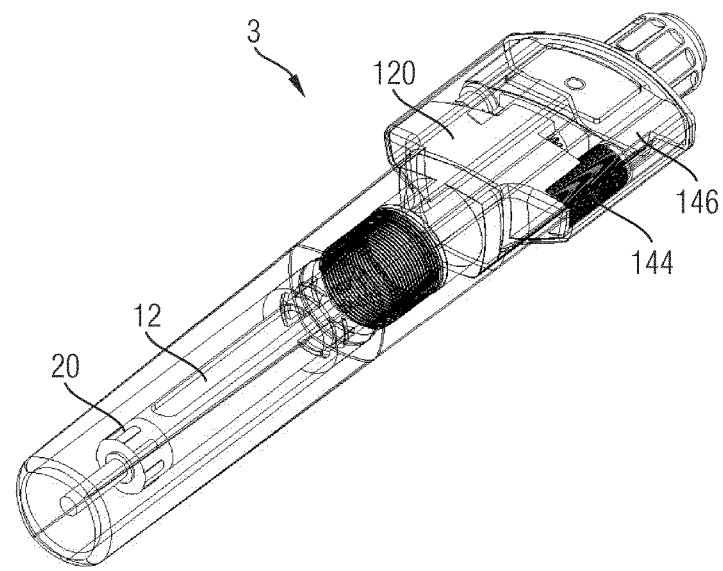
FIG. 11 shows a partially transparent view through the assembled drug delivery device.

In FIGS. 1, 2 and 10 the drive mechanism 3 of the drug delivery device 10 is illustrated in an assembled and in an exploded view, respectively. The drug delivery device 10 may be of pen-injector type and may comprise a substantially cylindrical and axially elongated shape. In the present set of Figures, the axial direction is denoted with reference number 1 and the opposite proximal direction is indicated by reference number 2. The drug delivery device 10 comprises a proximal housing component 30 to receive and to accommodate the drive mechanism 3 and in particular the functional and moveable components, the drive mechanism 3 is made of.

In distal direction 1, the housing 30 is connected with a cartridge holder 12 which is adapted to accommodate and to receive a cartridge 14 containing the medicament to be dispensed by the drug delivery device 10. The cartridge 14 typically comprises a vitreous barrel 18 of cylindrical shape which is sealed in distal direction 1 by a pierceable sealing member, such like a septum.

In proximal direction 2, the cartridge 14 is sealed by a piston 16 slidably arranged in the vitreous barrel 18 of the cartridge 14. Displacement of the piston 16 in distal direction 1 leads to a respective built-up of a fluid pressure inside the cartridge 14. When the distal outlet of a cartridge 14 is connected with e.g. a needle assembly 20, as shown in FIG. 1, a predefined amount of the liquid medicament contained in the cartridge 14 can be expelled and dispensed via an injection needle 25 of the needle assembly 22.

In FIG. 2 however, a needle cap 24 to protect the double-tipped injection needle 25 is indicated. The needle assembly 20 is typically arranged on a distal end portion of the cartridge holder 12. Typically, a distally located socket of the cartridge holder 12 and a needle hub 22 of the needle assembly 20 comprise mutually corresponding threads to screw the needle assembly 20 onto the cartridge holder 12 in a releasable and removable way.

The cartridge holder 12 and hence the cartridge 14 is to be protected and covered by a protective cap 26 which is shown in FIGS. 1 and 2. Prior to setting and/or dispensing of a dose, the protective cap 26 as well as the inner needle cap 24 are to be removed. After dispensing or injecting of the medicament into biological tissue, the needle assembly 20 is typically to be discarded and the distal end of the drug delivery device 10 is to be covered by the protective cap 26.

The drive mechanism 3 as illustrated in an exploded view in FIG. 10 and as shown in cross section in its fully assembled configuration in FIGS. 1 and 2 comprises numerous functional components by way of which a dose of variable size can be set and subsequently dispensed.

The dose dispensing procedure comes along with a distally directed advancing displacement of the piston rod 90 relative to the housing 30. The drive mechanism 3 therefore comprises at least a housing 30, a piston rod 90, a drive wheel 80 or drive nut and a drive sleeve 40 which can be selectively and operably coupled for setting and dispensing of a dose, respectively.

The dose dispensing procedure comes along with a distally-directed advancing displacement of the piston rod 90 relative to the housing 30. As illustrated for instance in FIG. 2, the piston rod 90 comprises an outer thread 91 which is typically rotably locked to a radially inwardly extending support 34 of the housing 30. Advancing of the piston rod 90 in distal direction relative to the housing 30 is typically achieved by a rotation of the drive wheel 80 threadedly engaged with the piston rod 90 and beeing axially fixed in the housing 30.

In the following, setting of a dose is described.

For setting of a dose, a user typically takes the drug delivery device 10 and starts to rotate the proximally located dose setting member 85 relative to the proximal housing 30. Here, the dose setting member 85 comprises a dose dial, which is axially fixed to the housing 30 and which may be arbitrarily dialled either clockwise or counter-clockwise for incrementing and decrementing a dose to be set accordingly.

Figure 3:
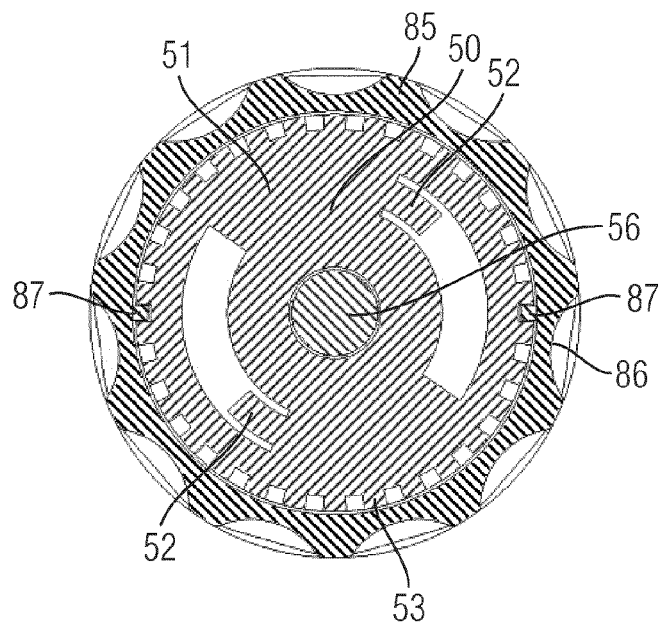
FIG. 3 shows a cross-section along A-A according to FIG. 2.

As in particular illustrated in FIG. 3, the dose setting member 85 comprises a rippled structure 86 at its outer circumference, which allows and supports a slip-free gripping and dialling thereof. Moreover, the dose setting member 85 has the form of a hollow sleeve and features two diametrically oppositely located and radially inwardly extending protrusions 87 engaging with a toothed geared rim 53 of a proximal clutch member 50 being rotatably supported in the housing 30.

As further illustrated in FIGS. 1 and 2, the housing 30 comprises a proximal closure or lid 32 which is axially intersected by the dose setting member 85, by the proximal clutch member 50 and by a dose dispensing button 55 proximally protruding from the dose setting member 85. As further indicated in FIGS. 1, 2 and in FIGS. 20, 21, the dose setting member 85 comprises a distally extending projection 88 of rim or ring-like shape extending into or through the proximal closure 32 of the housing 30. By means of the projection 88, the dose setting member 85 may be axially fixed to the housing 30.

The proximal clutch member 50 comprises or forms an axially extending shaft portion to axially and rotatably engage with a main clutch member 60 featuring a sleeve-like geometry. The proximal clutch member 50 typically comprises a fastening or fixing element 54 at its distal end of its shaft portion to rotatably and to axially engage with the main clutch member 60. In this way, a rotation of the proximal clutch member 50 typically induced by dialling of the dose setting member 85 can be equally and directly transferred into a respective rotation of the main clutch member 60.

Figure 5:
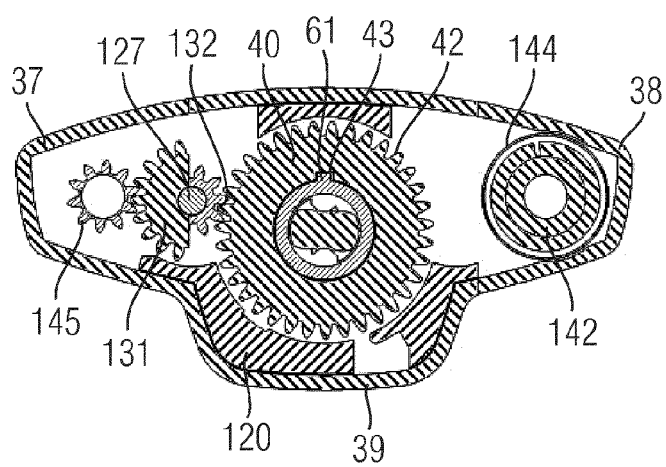
FIG. 5 shows a cross-section along C-C according to FIG. 2.
Figure 6:
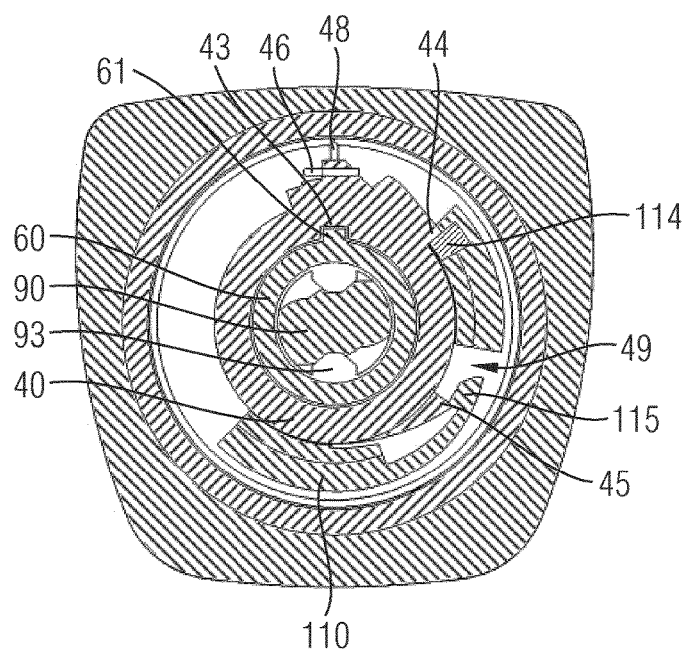
FIG. 6 shows a cross-section along D-D according to FIG. 2.

The main clutch member 60 is rotatably engaged with the drive sleeve 40 adapted to accommodate both, a distal end of the proximal clutch member 50 and almost the entirety of the main clutch member 60 extending almost all the way through the drive sleeve 40 in distal direction 1. As shown in FIGS. 5 and 6, the main clutch member 60 comprises a radially outwardly and axially extending ridge or protrusion 61 serving as a fastening element to rotatably engage with a correspondingly shaped groove or notch 43 provided at an inside facing portion of the drive sleeve 40.

By means of the radially outwardly extending protrusion 61 of the main clutch member 60 and the correspondingly shaped groove 43 of the drive sleeve 40, a splined engagement of main clutch member 60 and drive sleeve 40 can be provided. Consequently, the drive sleeve 40 and the main clutch member 60 are rotatably locked but the main clutch member 60 is free to be displaced in axial direction 1, 2 relative to the drive sleeve 40.

Figure 12:
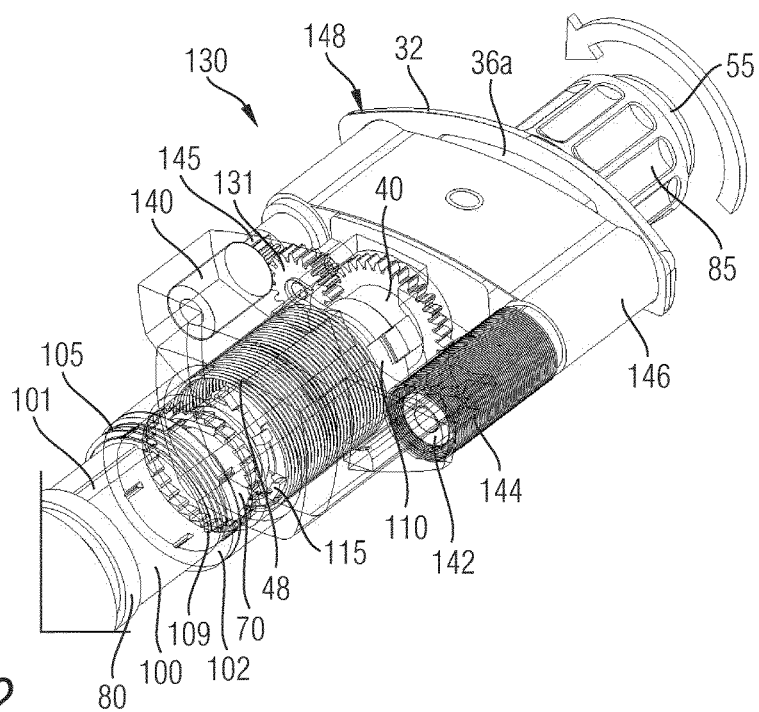
FIG. 12 is a perspective view of the dose indicating mechanism.

As illustrated in FIGS. 6 and 12 the drive sleeve 40 is connected with one end of a helical spring 48 extending around and enclosing the distal portion of the drive sleeve 40. The opposite end of the spring 48 is connected to an insert 120 which is fixedly connected to the housing 30. In this way, the drive sleeve 40 is rotatable in a dose incrementing direction 4 against the action of the helical spring 48.

Figure 9:
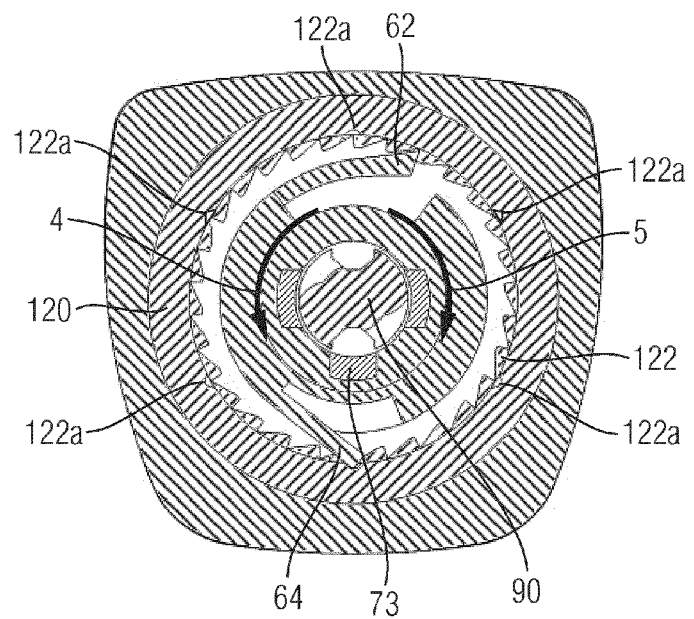
FIG. 9 shows a cross-section along G-G according to FIG. 2.

As further shown in FIG. 9 a pawl-like and radially outwardly extending ratchet member 62 is adapted to engage with a toothed ring portion 122 of the insert 120. The toothed ring 122 comprises a saw tooth profile such that the radially outwardly biased ratchet member 62 of the main clutch member 60 consecutively and stepwise engages with the toothed ring 122 in order to store and save mechanical energy of the strained helical spring 48 during a dose setting procedure. Here, the main clutch member 60 and the drive sleeve 40 rotatably locked therewith can be rotated in a dose incrementing direction 4 in discrete steps, e.g. corresponding to an international unit in case of a drug delivery device adapted for administering of insulin.

The engagement of the ratchet member 62 and the toothed ring 122 is such, that also a dose decrementing rotation 5 is possible when a respective torque is applied to the dose setting member 85 and hence to the main clutch member 60. The toothed flanks of the ratchet member 62 and the teeth of the toothed ring 122 are designed such, that also a well-defined and precise dose decrementing rotation of the main clutch member 60 and hence of the drive sleeve 40 is possible, in particular for correcting and for decrementing a dose that would be too large otherwise.

Figure 13:
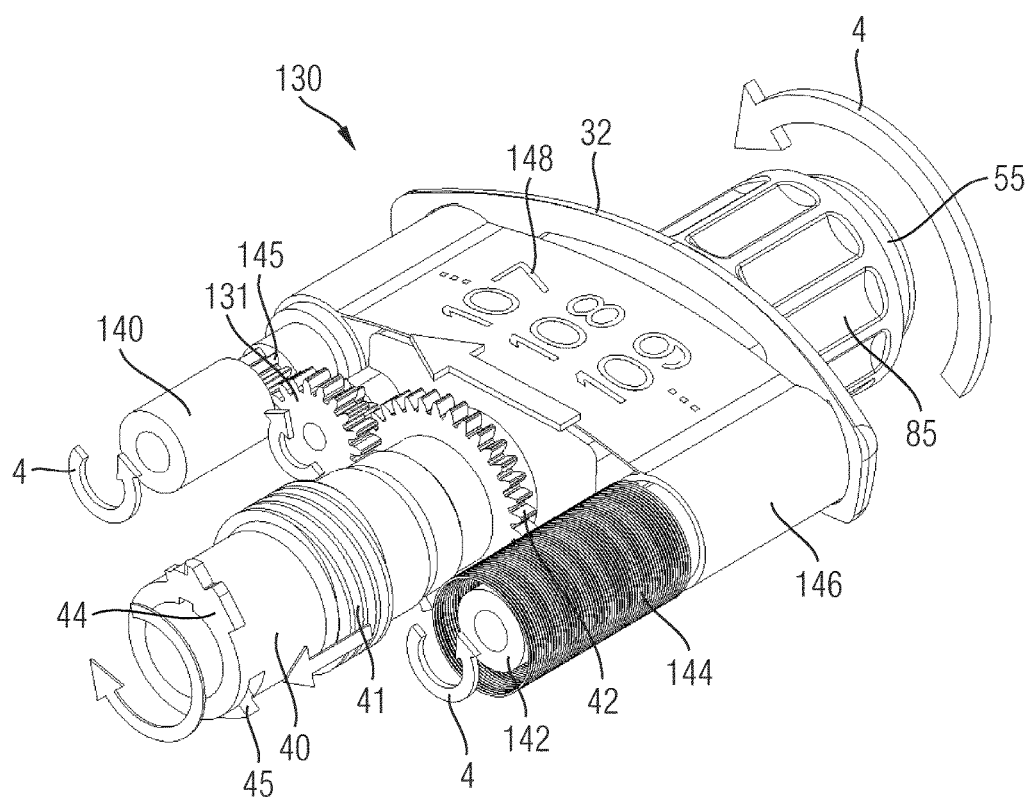
FIG. 13 shows an isolated view of the dose indicating mechanism.

As for instance illustrated in FIGS. 6, 7 and 12, 14 and 15 there is also provided a dose limiting member 110 acting as a single dose limiting member during a dose setting procedure. The dose limiting member 110 is threadedly engaged with the drive sleeve 40. As illustrated in FIG. 13, the drive sleeve 40 comprises only a limited axial portion provided with an outer thread 41. Said outer thread 41 is located offset from a distal end as well as from a proximal end of the drive sleeve 40. Adjacent to the threaded portion 41, the outer circumference of the drive sleeve 40 is rather smooth shaped.

Figure 7:
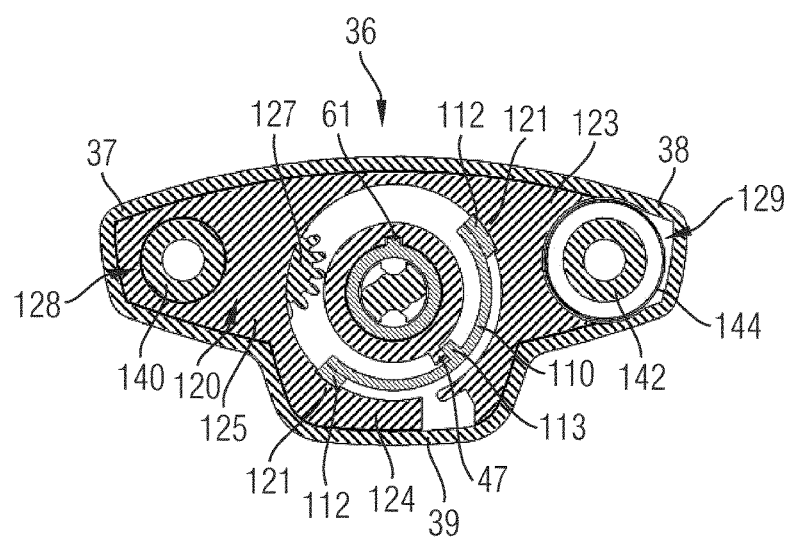
FIG. 7 shows a cross-section along E-E according to FIG. 2.

As shown in FIGS. 6 and 7, the dose limiting member 110 is of shell-like shape and extends only partially around the outer circumference of the drive sleeve 40. As further illustrated in FIG. 6, a distal end of the dose limiting member 110 extends radially between the drive sleeve 40 and the helical spring 48. Moreover, the distal end of the drive sleeve 40 comprises a radially outwardly extending spring mount 46 to engage with the distal end of the helical spring 48.

Figure 14:
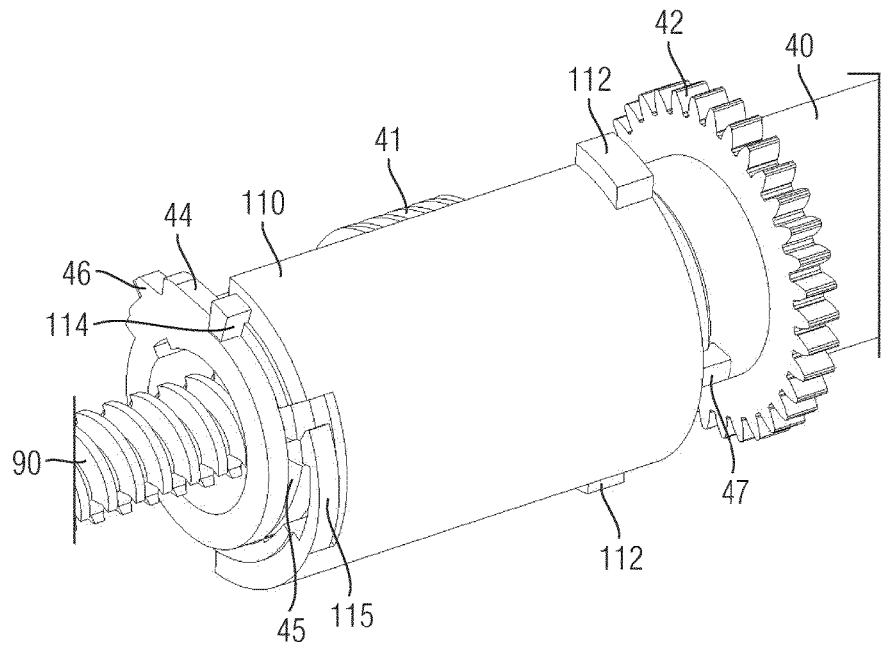
FIG. 14 shows the dose limiting member in a zero dose configuration on the drive sleeve.
Figure 15:
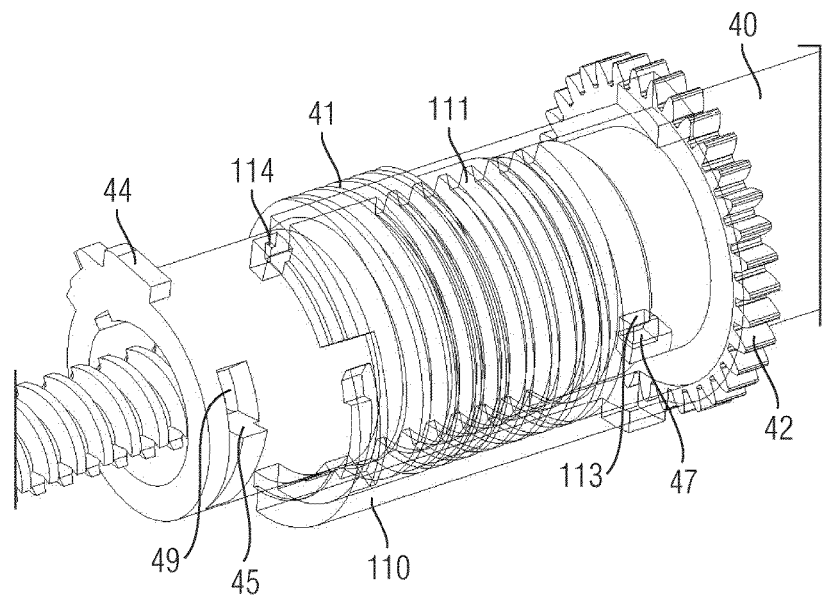
FIG. 15 shows the dose limiting member according to FIG. 14 in a maximum dose configuration.
Figure 16:
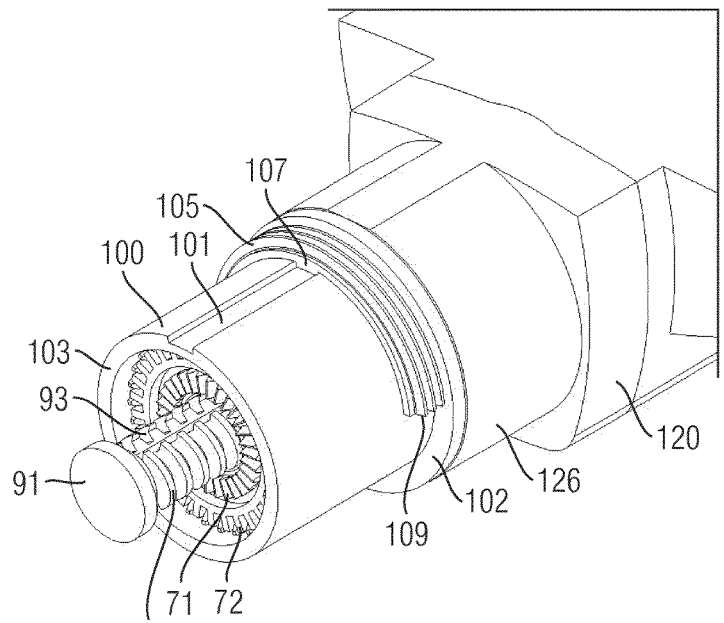
FIG. 16 shows a perspective view of a last dose limiting mechanism.

According to FIG. 15, the dose limiting member 110 comprises an inner thread 111 to engage with the outer threaded portion 41 of the drive sleeve 40. As further illustrated in FIGS. 7 and 14 the dose limiting member 110 comprises two diametrically oppositely located radially outwardly extending protrusions 112 engaging with correspondingly formed recesses 121 of the insert 120.

The cross-section according to FIG. 7 further illustrates that the insert 120 almost entirely fills the interior volume of the surrounding housing 30. Therefore, the insert 120 is fixedly connected to the housing 30 and serves as a housing portion to provide a mounting base for various functional components of the drive mechanism 3.

By means of mutually engaging protrusions 112 and grooves 121 the dose limiting member 110 is rotatably locked to the insert 120 and hence to the housing 30.

Figure 24:
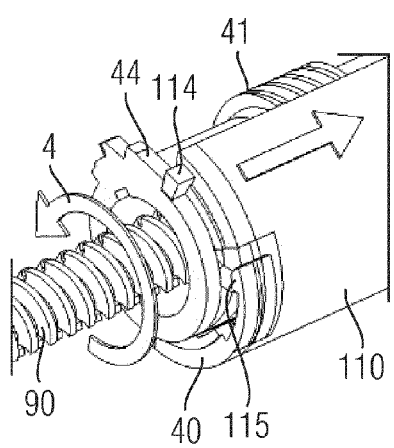
FIG. 24 is a perspective view of the dose limiting member at the beginning of a dose incrementing displacement.
Figure 24A:
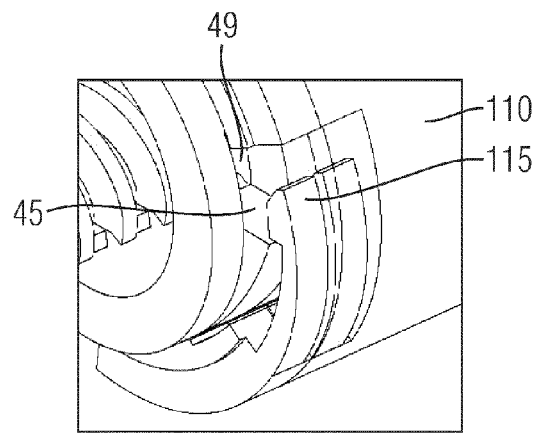
FIG. 24a shows the clicking member of the dose limiting member according to FIG. 24.
Figure 25:
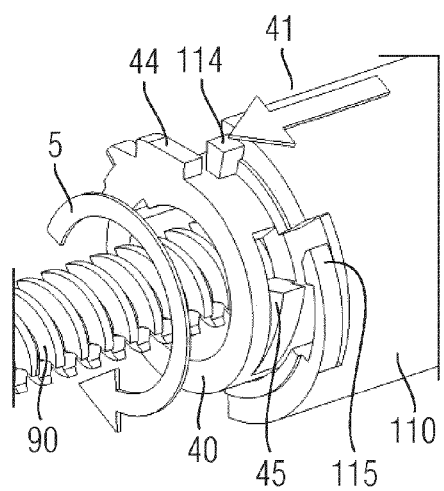
FIG. 25 shows the dose limiting member during a dose decrementing displacement.
Figure 25A:
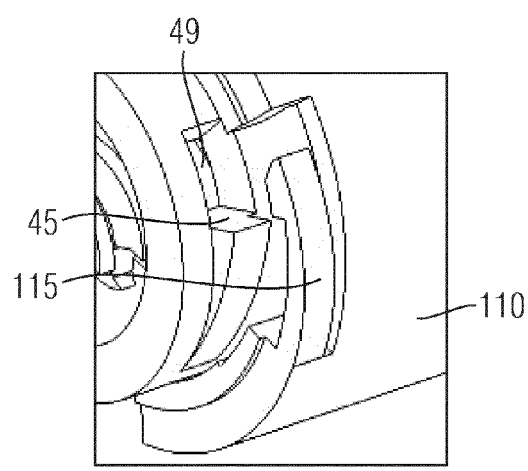
FIG. 25a shows an enlarged view of the clicking member of the dose limiting member according to FIG. 25.

Moreover, since the dose limiting member 110 is also threadedly engaged with the drive sleeve 40, a rotation of the drive sleeve 40 in dose incrementing direction 4, as illustrated in FIG. 24 leads to a proximally directed displacement of the dose limiting member 110. An oppositely directed rotation of the drive sleeve 40 in dose decrementing direction 5 leads to a respective opposite, hence distally directed displacement of the dose limiting member 110 relative to the insert 120, the housing 30 and relative to the drive sleeve 40 as illustrated in FIG. 25.

Moreover, FIGS. 7, 12, 14 and 15 show that the dose limiting member 110 comprises a radially inwardly extending first stop 113 near its proximal end which is adapted to circumferentially abut with a correspondingly shaped but radially outwardly extending first stop 47 of the drive sleeve 40. The configuration as indicated in FIGS. 7 and 15 may relate to a maximum dose configuration, in which the mutual abutment of first stops 47, 113 of drive sleeve 40 and dose limiting member 110 inhibits a further rotational displacement of the drive sleeve 40 in dose incrementing direction 4. In this way, a maximum dose for a single dose dispensing procedure can be effectively limited.

Later on and during dose dispensing or during dose correction, i.e. when the drive sleeve 40 is rotated in a dose decrementing direction 5, the dose limiting member 110 will be displaced in distal direction 1 in order to return into its initial zero dose configuration as it is indicated for instance in FIG. 14. Also here, mutually corresponding second stops 44, 114 of drive sleeve 40 and dose limiting member 110 are provided. While the second stop 44 of the drive sleeve 40 extends radially outwardly from a distally located rim of the drive sleeve 40 the second stop 114 of the dose limiting member 110 is located at a distal and circumferential edge of the shell-shaped dose limiting member 110. In particular, the second stop 114 is provided at a leading edge with respect to a rotation in dose decrementing direction 5.

In contrast to that, the first and radially inwardly extending stop 113 of the dose limiting member 110 extends substantially midway between the diametrically oppositely located radially outwardly extending protrusions 112. Moreover, the protrusions 112 and the first stop 113 are located in a common transverse plane as indicated in FIG. 7.

In this way, forces or torque introduced into the dose limiting member 110 via the rotating drive sleeve 40 can be smoothly and directly transferred to the insert 120.

Since the dose limiting member 110 almost completely extends through the helical spring 48 in axial direction a rather compact and space saving arrangement for the dose limiting member 110 can be attained.

As further illustrated for instance in FIG. 12 the drive mechanism 3 also comprises a dose indicating mechanism 130 featuring first and second spools 140, 142 rotatably supported in the housing 30 and being oriented substantially parallel to each other as well as being oriented substantially parallel to the drive sleeve 40 and the piston rod 90 extending therethrough. The two spools 140, 142 are further mutually connected by means of a dose indicating tape 146 having several numbers 148 printed thereon.

As shown in FIGS. 2 and 12 the first spool 140 is rotatably engaged with the drive sleeve 40 by means of a series of gear wheels 42, 131. Here, the drive sleeve 40 comprises a gear wheel 42 that mates with a sprocket 132 of a gear wheel 131. Said gear wheel 131 is further geared and engaged with a corresponding gear wheel 145 of the first spool 140. In this way, a rotative movement of the drive sleeve 40 can be directly transferred into a roll off and roll up rotation of the first spool 140.

The second spool 142 is further engaged with a spool spring 144. In this way, unwinding or unrolling the dose indicating tape 146 from the second spool 142 may take place against the action of the spool spring 144. By means of the spool spring 144 the dose indicating tape 146 can be strained and can be kept substantially free of slack. Additionally and as shown in FIG. 12, the housing comprises a support 36a to provide a basis for the flexible dose indicating tape 146.

As further indicated in FIG. 2, the first spool 140 comprises a proximally located bobbin integrally formed with a distally located bearing portion 134. The bearing portion 134 is located and supported in a cup-shaped receptacle of the insert 120, thereby forming a bearing 128 for the first spool 140. In a corresponding way also the second spool 142 can be rotatably supported in the insert 120. As indicated in FIG. 7, the respective bearing portion 136 of the second spool 142 is only partially formed by an insert portion 123 of the insert 120.

The residual portion of the respective bearing 129 is formed directly from a radially outwardly extending receptacle portion 38 of the housing 30. As further indicated in FIGS. 2 and 7, the spool spring 144 radially extends between the outer circumference of the bearing portion 136, the inside facing sidewall portions of the insert portion 123 and the receptacle portion 38 of the housing 30.

As it is further illustrated in FIG. 7, the drug delivery device 10 in an axial portion comprises a T-like shape in cross-section to accommodate the dose indicating mechanism 130, wherein the two spools 140, 142 are located in receptacle portions 37, 38 being furthest away from each other. Therebetween and on one side there extends a radially outwardly extending receptacle portion 39 of the housing 30. Opposite the receptacle portion 39, the housing 30 comprises a dose indicating window 36 through which the numbers 148 of the dose indicating tape 146 can be visualised.

The lobe-shaped receptacle portions 37, 38 and 39 of the housing 30 are almost entirely occupied with correspondingly shaped insert portions 125, 123 and 124 of the insert 120, respectively.

Here, the insert 120 may provide a mounting basis to preassemble the dose indicating mechanism 130 and to insert the entire dose indicating mechanism 130 in one step into the housing 30 during assembly of the drug delivery device 10.

As further indicated in FIG. 5, also the gear wheel 131 is rotatably supported by a pin-shaped bearing 127 of the insert 120.

As further shown in FIGS. 2 and 10, the proximal closure 32 of the housing 30 provides axial fixing of the two spools 140, 142 inside the housing 30. Hence, the two spools 140, 142 can be axially constrained by the insert 120 and by the proximal closure 32 of the housing 30.

In FIGS. 2, 12 and in FIGS. 16 to 20 a last dose sleeve 100 rotatably supported in the housing 30 is shown. The last dose sleeve 100 comprises a radially outwardly extending flange portion 102 by way of which the last dose sleeve 100 axially abuts with a proximal sleeve portion 126 of the insert 120. Moreover, the last dose sleeve 100 comprises an axially extending groove 101 intersecting a rather smooth shaped outer circumference thereof.

Said groove 101 is engaged with a radially inwardly extending protrusion 107 of a last dose member 105, which is designed as a last dose nut or as a half nut. As for instance indicated in FIG. 18 the last dose member 105 comprises a semi-circular arcuate shape and features radial stop faces 108, 109 at its opposite circumferential ends. Moreover, the last dose member 105 comprises an outer thread 106 to threadedly engage with a correspondingly shaped threaded portion 33 of the housing 30. In this way, the last dose limiting member 105 is threadedly engaged with the housing 30 but is rotatably locked to the last dose sleeve 100.

Figure 4:
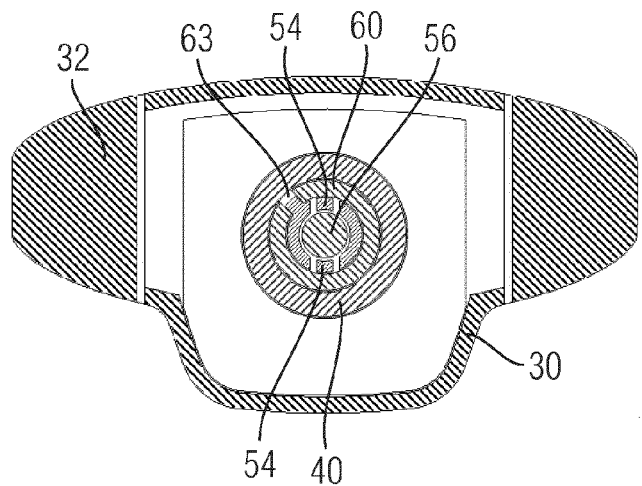
FIG. 4 shows a cross-section along B-B according to FIG. 2.
Figure 22:
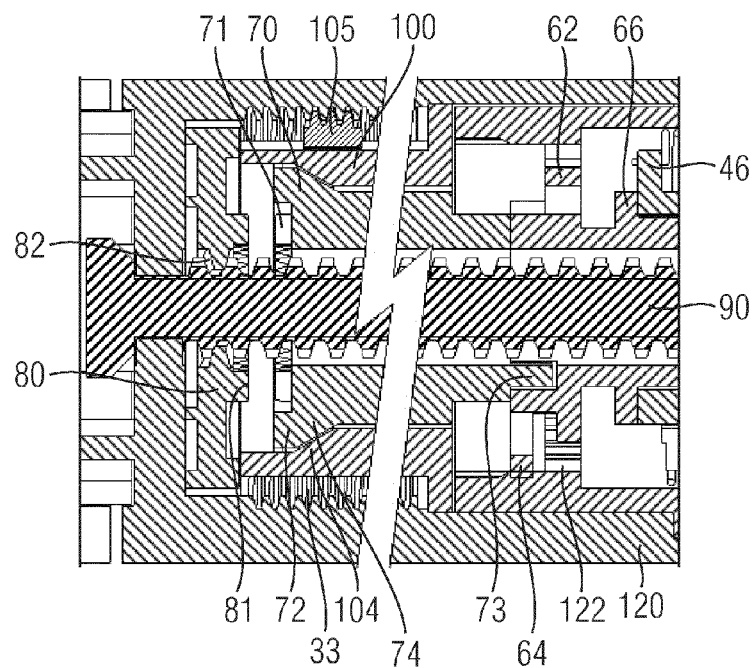
FIG. 22 shows a longitudinal cross-section through a distal clutch member in dose setting configuration.
Figure 23:
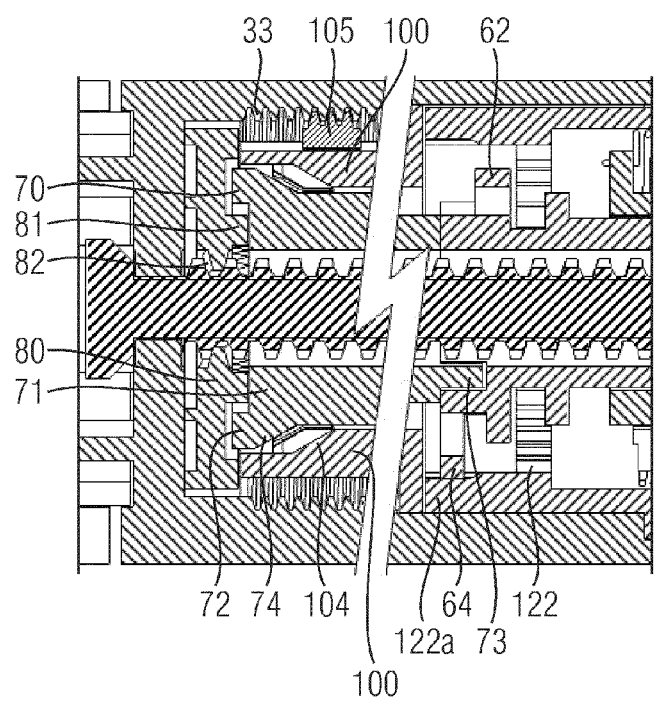
FIG. 23 shows a longitudinal cross-section of the distal clutch member in a dose dispensing configuration.

In FIGS. 1, 22 and 23 a distal clutch member 70 is illustrated, which is axially as well as rotatably engaged with the main clutch member 60. Hence, a rotation of the main clutch member 60 equally transfers to the distal clutch member 70. Moreover, also an axial displacement of the main clutch member 60 relative to the housing 30 or relative to the drive sleeve 40 is equally transferrable to a respective axial displacement of the distal clutch member 70. In order to provided axial and rotational engagement between the main clutch with the distal clutch 70 and/or with the proximal clutch 50 the main clutch 60 may further exhibit a notch or groove 63 as shown in FIG. 4 to engage with a correspondingly shaped snap member of e.g. the proximal clutch 50, which is not particularly illustrated. Moreover and as indicated in the cross sections of FIGS. 9 and 22 the distal clutch member 70 comprises three circumferentially distributed snap elements 73 to axially engage with correspondingly shaped recesses of the main clutch 60.

Figure 8:
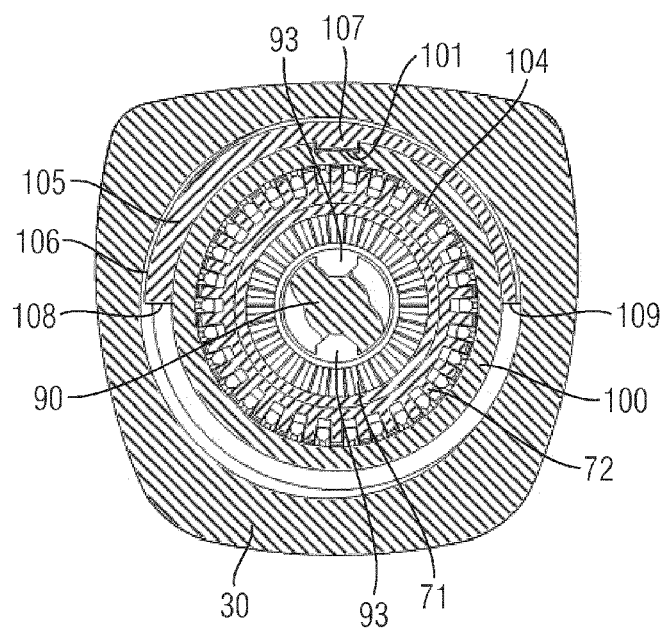
FIG. 8 shows a cross-section along F-F according to FIG. 2.

In a dose setting configuration as illustrated in FIG. 22, the distal clutch member 70 is rotatably locked to the last dose sleeve 100. As shown for instance in cross-section according to FIG. 8, the distal clutch member 70 comprises radially outwardly extending teeth 72 engaging with a correspondingly shaped toothed structure 104 at an inside facing sidewall portion of the last dose sleeve 100. In this way, a rotation of the drive sleeve 40 and hence a rotation of the clutch members 50, 60, 70 can transfer to a respective rotation of the last dose sleeve 100.

As a consequence, the last dose member 105 will travel in axial direction relative to the last dose sleeve 100 during a dose setting procedure. The lead of the threaded engagement of the last dose member 105 and the housing 30 as well as the axial elongation of the last dose sleeve 100 is designed such that a stop configuration as for instance illustrated in FIG. 19 correlates with the maximum allowable distal position of the piston rod 90 relative to the barrel 18 of the cartridge 14.

Figure 19:
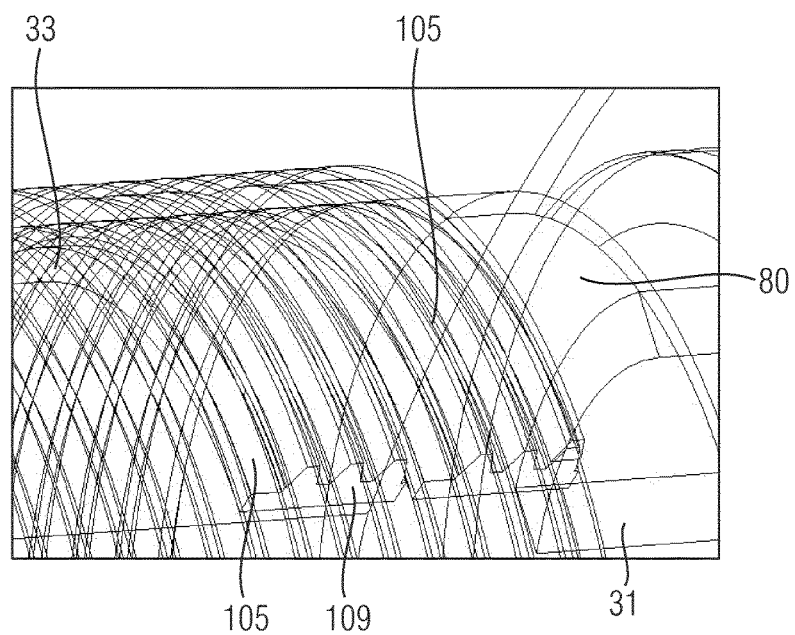
FIG. 19 shows a configuration of the last dose limiting mechanism in a last dose configuration.

In FIG. 19 mutual abutment of one of the stop faces 108, 109 with a radially inwardly extending stop 31 of the housing 30 is shown. Also here and in comparison with the single dose limiting member 110 radially extending stops 108, 109, 31 may provide a well-defined blocking of the mutually engaging components 105, 110 and housing 30.

Since the last dose sleeve 100 is only selectively coupled with the drive sleeve 40 and/or with the distal clutch member 70 during a dose setting procedure, the last dose member 105 will always rest in its axial position during a dose dispensing procedure.

Hence, during consecutive dose setting procedures, the last dose member 105 successively advances towards a last dose limiting configuration. In situations where the amount of medicament left in the cartridge 12 is less than the size of a single dose to be set during a dose setting procedure, the last dose limiting member 105 will be advanced in distal direction 1 and will engage with the radial stop 31 of the housing 30 thereby blocking a further rotation of the last dose sleeve 100 and hence of the clutches 50, 60, 70 and the dose setting member 85, accordingly. In this way it can be effectively prevented that a user selects and dials a dose exceeding the amount of medicament left in the cartridge 14.

In the following, dispensing of a dose is described.

Figure 17:
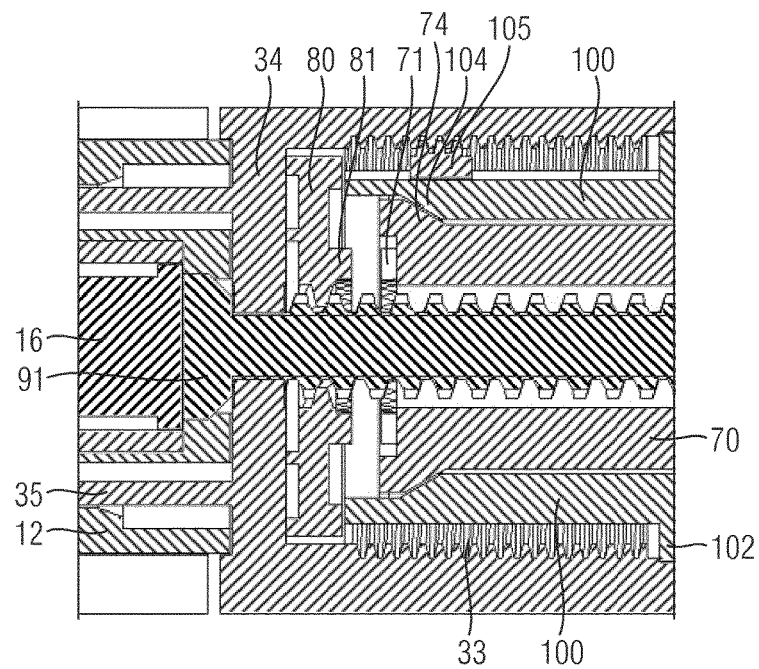
FIG. 17 shows an enlarged longitudinal cross-section through the last dose limiting mechanism.
Figure 18:
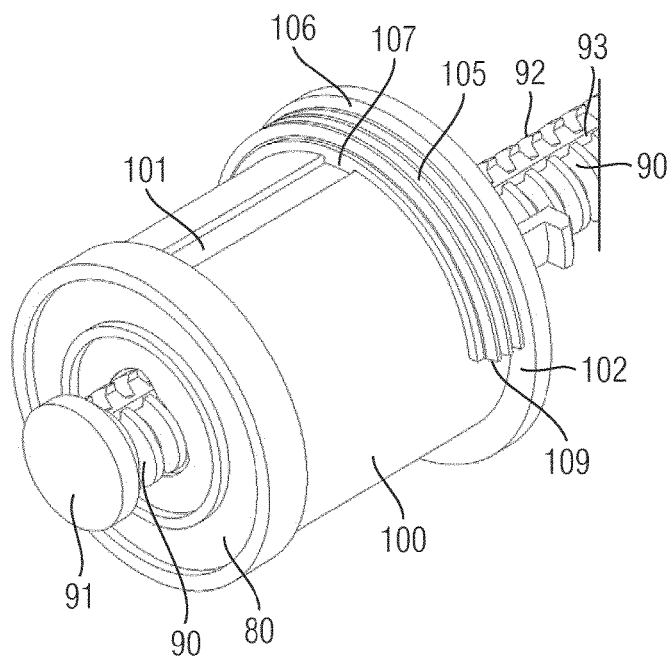
FIG. 18 shows another perspective view of the last dose limiting mechanism in a zero dose configuration.

As shown in FIG. 17, the piston rod or lead screw 90 operably engaged with a proximal end face of the piston 16 of the cartridge 14 is axially guided by the radially inwardly extending support 34 or web of the housing 30. As shown in cross section in FIG. 8, the piston rod 90 not only comprises an outer thread 92 but also two diametrically opposite and axially extending grooves 93. By means of said grooves 93 the piston rod 90 is rotatably locked to the housing 30. Hence, the piston rod 90 is splined to the housing 30. The piston rod 90 further comprises a radially widening pressure piece 91 or a pressure foot at its distal end in order to homogeneously transfer axially directed thrust to the piston 16 of the cartridge 14 during dose dispensing.

The piston rod 90 is further threadedly engaged with a drive wheel 80 comprising an inner thread 82 engaged with the outer thread 92 of the piston rod 90. Due to the threaded engagement with the drive wheel 80 and the splined engagement with the housing 30, the piston rod 90 experiences a distally directed translational displacement when the drive wheel 80 rotates in a dose decrementing direction 5 during dose dispensing. In order to transfer a dose dispensing torque to the drive wheel 80 or drive nut the drive wheel 80 comprises a crown wheel portion 81 at its proximally facing side to engage with a correspondingly shaped crown wheel portion 71 of the distal clutch member 70.

By displacing the distal clutch member 70 in distal direction 1 the mutually corresponding crown wheel portions 71, 81 of distal clutch member 70 and drive wheel 80 mutually engage. In this way, a rotation of the distal clutch member 70 can be equally transferred to a rotation of the drive wheel 80, which transfers to a distally directed displacement of the piston rod 90.

Figure 20:
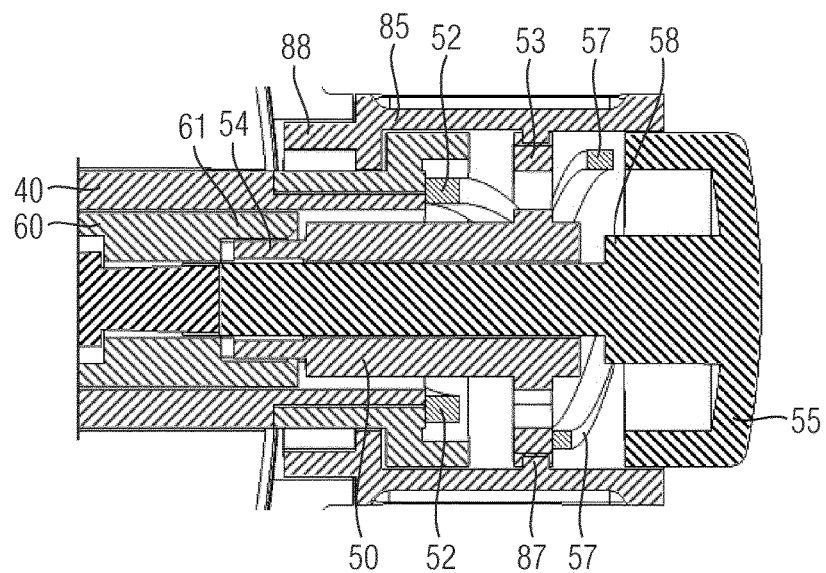
FIG. 20 shows a longitudinal cross-section through the proximal end of the drive mechanism in a dose setting configuration.
Figure 21:
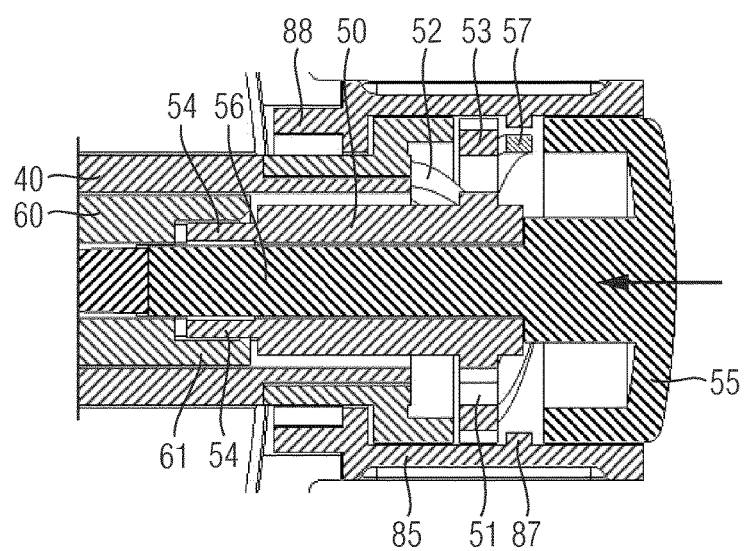
FIG. 21 shows a proximal end of the drive mechanism in a dose dispensing configuration.

A distally direction displacement of the distal clutch member 70 can be attained by depressing the dose dispensing button 55 in distal direction 1 as indicated by a comparison of FIGS. 20 and 21. The dose dispensing button 55 comprising a shaft portion 56 extending into the hollow shaft portion of the proximal clutch member 50 is displaceable in distal direction 1 until a stepped portion 58 radially outwardly extending from the shaft portion 56 axially abuts with a proximal end of the proximal clutch member 50.

In this way, axially and distally directed displacement of the dose dispensing button 55 against the action of an integrated spring 57 can be transferred into a respective distally directed displacement of the mutually engaging clutch members 50, 60 and 70. Since the clutch members 50, 60 and 70 are axially engaged in both directions, the proximal clutch member 50 can be displaced in distal direction 1 against the action of another integrated spring 52, which axially abuts with a proximal end face of the drive sleeve 40 and/or with a stepped portion of the dose setting member 85.

Distally directed displacement of the proximal clutch member 50 relative to the dose setting member 85 also disengages the protrusions 87 and the geared rim 53. In the dose dispensing configuration as shown in FIG. 21, the dose setting member 85 is therefore substantially functionless. It may be rotated in any direction without having connection to the proximal clutch member 50.

The proximal clutch member 50 is depressible in distal direction 1 against the action of the spring 52. Since the proximal clutch member 50 is axially engaged with the main clutch member 60, e.g. by means of a snap fit engagement, and since the main clutch member 60 is also axially connected with the distal clutch member 70, a release of the dose dispensing button 55 allows and induces a proximally directed return motion of the proximal clutch member 50 under the effect of the relaxing spring 52.

In this way, the distal clutch member 70 can be selectively engaged and disengaged with the drive wheel 80. Moreover, by means of the integrated spring 57 also the dose dispensing button 55 will return into its initial proximal end configuration in which the dose dispensing button 55 at least partially extends from the proximal end face of the dose setting member 85.

As shown in FIG. 20, the integrated spring 57 of the dose dispensing button 55 axially abuts against a radially outwardly extending flange portion 51 of the proximal clutch member 50.

By means of a distally directed displacement of the distal clutch member 70 the distal clutch member 70 not only rotatably locks to the drive wheel 80 but also disengages from the last dose sleeve 100 as becomes apparent from a comparison of FIGS. 22 and 23. As illustrated there, the distal clutch member 70 comprises an inclined or tapered toothed structure 104 at its inner circumference near its distal end.

Accordingly, the last dose sleeve 100 comprises a correspondingly shaped inclined toothed portion 74 to engage with the toothed portion 104 of the last dose sleeve 100 when in dose setting configuration, hence when the distal clutch member 70 is in its proximal stop position.

As further indicated in FIG. 22 the ratchet member 62 of the main clutch 60 is rotatably locked to the toothed ring portion 122 of the insert 120. Additionally and as shown in FIG. 22 the main clutch 60 comprises a radially outwardly extending flange 66 which serves as a stop to engage with a distal end face of the drive sleeve 40. In this way the proximally directed displacement of the main clutch 60 under the effect of the springs 52, 57 can be delimited.

By displacing the three clutch members 50, 60, 70 simultaneously in distal direction 1, the crown wheel portion 71 of the distal clutch member 70 will engage with the corresponding crown wheel portion 81 of the drive wheel 80 before the ratchet member 62 disengages from the toothed ring portion 122 of the insert 120. The mutual engagement of the two crown wheel portions 71, 81 is designed such, that at least a further distally directed displacement of the distal clutch member 70 towards the drive wheel 80 is still possible when the distal clutch member 70 and the drive wheel 80 are already rotatably coupled.

During this further distally directed displacement of the distal clutch member 70 and when reaching the distal stop configuration, the ratchet member 62 displaces or has displaced in distal direction 1 relative to the toothed ring 122 and is then no longer inhibited to rotate under the action of the relaxing helical spring 48. As indicated in FIG. 23, the ratchet member 62 is disengaged from the insert 120 and hence it is effectively released from the housing 30.

The main clutch member 60 further comprises a pawl-shaped clicking member 64 as illustrated in FIGS. 9 and 23. Said clicking member 64 is arranged axially offset from the ratchet member 62. It may engage with another recessed structure 122a featuring numerous and equidistantly arranged recesses 122a located on the inside facing wall of the insert 120 when reaching the dose dispensing configuration as illustrated in FIG. 23.

The clicking member 64 is oriented symmetrically to the ratchet member 62 and engages with the recess structure 122a when the ratchet member 62 disengages from the toothed ring 122. Since the main clutch member 60 is now allowed to rotate in a dose decrementing direction 5 the clicking member 64 is operable to generate a frequent clicking sound when meshing with the recessed structure 122a, thereby audibly indicating to a user, that a dose dispensing procedure is in progress.

Moreover the clicking member 64 and the recessed structure 122a of the insert 120 may be shaped and designed in such a way that only a rotation in dose decrementing direction 5 is allowed while an oppositely directed rotation in dose incrementing direction 4 of the distal clutch 60 relative to the insert 120 and hence relative to the housing 30 is effectively blocked. In this way the clicking member 64 and the recessed structure 122a act as a further ratchet mechanism operable to impede a proximally directed displacement of the piston rod 90.

In order to provide a substantially slipless switching from dose setting mode to the dose dispensing mode and vice versa, the distal clutch member 70 engages with the drive wheel 80 before the main clutch member 60 disengages from the insert 120 or housing 30. Also in the event of a premature release of the dose dispensing button 55 during a dose dispensing procedure, a rotational interlock of the main clutch member 60 with the insert 120 will be re-established before distal clutch member 70 and drive wheel 80 become operably disengaged.

Since the drive sleeve 40 rotates in dose decrementing direction 5 during dose dispensing also the dose limiting member 110 will return into its initial configuration, i.e. in a zero dose configuration, in which the second stop 114 of the dose limiting member 110 engages with a radially extending second stop 44 of the drive sleeve 40.

Moreover, and as shown in FIG. 6, the dose limiting member 110 comprises a circumferentially extending clicking member 115 operable to audibly engage with a ledge 45 provided at a recess 49 of the drive sleeve 40. Here, the pawl-like clicking member 115 is biased radially inwardly so as to generate a click sound before or just when a zero dose configuration as illustrated in FIG. 6 is reached. Since the dose limiting member 110 travels in proximal direction 2 during dose incrementing rotation and travels in distal direction 1 during dose dispensing the audible click sound provided by the mutual engagement of the clicking member 115 with the ledge 45 is indicative to a user, that a dose dispensing procedure just terminates.

Accordingly and since the drive sleeve 40 is permanently engaged with the gear wheel 145 of the respective dose indicating mechanism 130, the numbers 148 of the dose indicating tape 146 that show up in the dose indicating window 36 will continuously count down until a zero dose configuration coinciding with the mutual engagement of the second stops 114, 44 is reached.

Moreover, as can be seen from the longitudinal cross-section according to FIG. 2, the drive wheel 80 is axially constrained between the radially inwardly extending protrusions 34 or of the housing and the last dose sleeve 100, which itself is in axial abutment with the distal sleeve portion 126 of the insert 120. In this way, fixing of the insert 120 in the housing 30 effectively fixes the last dose sleeve 100 and the drive wheel 80 in axial direction inside the housing 30.

Moreover, the insert 120 itself can be axially fixed in the housing 30 by means of the two spools 140, 142 extending axially between the bearing portion 128, 129 of the insert 120 and the proximal closure 32 of the housing 30.

As further shown in FIGS. 2 and 17, the housing 30 also comprises a distally extending appendix 35 extending in distal direction from the radially inwardly extending support 34. As indicated in FIG. 17, said appendix 35 may be operable to connect the proximal housing 30 with the cartridge holder 12. Cartridge holder 12 and housing 30 may either be releasably connected in order to provide a reusable drug delivery device, allowing to replace an empty cartridge 14 by a new one.

Alternatively, the drug delivery device 10 may also be designed as a disposable device, wherein cartridge holder 12 and proximal housing 30 are typically inseparably connected.

The present design and assembly of the components of the drive mechanism 3 allow for an axial adjustment of the piston rod 90 during a final step of assembly. In particular, prior to a final assembly of the dose dispensing button 55, effectively closing the housing 30 in proximal direction 2, the piston rod 90 is accessible by e.g. introducing an adjustment rod (not illustrated) through the hollow assembly of proximal clutch 50 and main clutch 60. In this way the piston rod 90 can be pushed in distal direction 1 to get in direct abutment with the piston 16 of the cartridge 14. In this way a conventional priming procedure typically to be executed by the end user prior to an initial use of the device 10 may become substantially superfluous.

The invention claimed is:

1. A drive mechanism of a drug delivery device for dispensing a dose of a medicament, the drive mechanism comprising:
   a housing comprising a radial stop,
   a piston rod to operably engage with a piston of a cartridge to displace the piston in a distal direction along a longitudinal axis of the housing,
   a last dose sleeve rotatably supported in the housing and being selectively engageable with a user operable dose setting member for setting of the dose, wherein the last dose sleeve is configured to be coupled to the dose setting member during dose setting and to be decoupled from the dose setting member during dose dispensing, wherein the last dose sleeve is axially fixed relative to the housing, and a last dose member threadedly engaged to and rotatable relative to the housing, rotationally locked to the last dose sleeve, and axially displaceable relative to the last dose sleeve, wherein the last dose member comprises a radial counter stop configured to engage with the radial stop to prevent rotation of the last dose member, wherein the last dose sleeve is hollow, and at least one axially extending clutch member extending through the last dose sleeve is axially displaceable relative to the last dose sleeve for selectively engaging the dose setting member with the last dose sleeve exclusively during the dose setting.

2. The drive mechanism according to claim 1, wherein the last dose member is radially sandwiched between the housing and the last dose sleeve.

3. The drive mechanism according to claim 1, wherein the last dose member is arc-shaped and comprises an outer thread to engage with an inner thread of the housing.

4. The drive mechanism according to claim 1, wherein:
one of the last dose member and the last dose sleeve comprises an axially extending groove,
the other one of the last dose member and the last dose sleeve comprises a correspondingly shaped radially extending protrusion, and
the axially extending groove is configured to receive the correspondingly shaped radially extending protrusion to inhibit relative rotation between the last dose member and the last dose sleeve.

5. The drive mechanism according to claim 1, wherein the radial counter stop extends radially at a circumferential end and is configured to engage with the radial stop during rotation of the last dose member relative to the housing, wherein the radial stop extends radially at an inside facing portion of the housing.

6. The drive mechanism according to claim 1, wherein the last dose sleeve comprises a radially outwardly extending flange portion at an axial end to support the last dose member in an initial assembly configuration.

7. The drive mechanism according to claim 1, wherein the last dose sleeve is axially constrained in the housing between a drive wheel and an insert axially fixed to the housing.

8. The drive mechanism according to claim 7, wherein the drive wheel is threadedly engaged with the piston rod, the piston rod being rotationally locked to the housing.

9. The drive mechanism according to claim 7, wherein the at least one axially extending clutch member is displaceable between a proximal stop position and a distal stop position, the at least one axially extending clutch member being engaged with the last dose sleeve in the proximal stop position such that torque is transferred from the at least one axially extending clutch member to the last dose sleeve and being engaged with the drive wheel in the distal stop position such that torque is transferred from the at least one axially extending clutch member to the drive wheel.

10. The drive mechanism according to claim 7, wherein the at least one axially extending clutch member comprises a crown wheel at its distal end face to engage with a corresponding crown wheel on a proximal end face of the drive wheel.

11. The drive mechanism according to claim 1, wherein the at least one axially extending clutch member comprises radially outwardly extending teeth at a distal end to selectively engage with correspondingly shaped radially inwardly extending teeth of the last dose sleeve.

12. The drive mechanism according to claim 1, wherein the at least one axially extending clutch member is axially displaceable in the distal direction against an action of a spring by means of a dose dispensing button located at a proximal end of the housing.

13. The drive mechanism according to claim 1, wherein the last dose member is configured to jointly rotate with the last dose sleeve and to move axially relative to the last dose sleeve during the dose setting.

14. The drive mechanism according to claim 1, wherein the last dose member and the last dose sleeve are configured to be axially fixed relative to the housing during the dose dispensing.

15. The drive mechanism according to claim 1, wherein the radial stop and the radial counter stop extend in both a radial direction and an axial direction, and the radial stop is configured to engage with the radial counter stop in a circumferential direction such that further rotation of the last dose sleeve and further rotation the last dose member are prevented when a last dose stop configuration of the drive mechanism has been reached.

16. A drug delivery device for dispensing a dose of a medicament, the drug delivery device comprising:
a housing comprising a radial stop;
a cartridge at least partially filled with the medicament and being arranged in the housing or in a cartridge holder fixed to the housing; and
a drive mechanism comprising
a piston rod to operably engage with a piston of the cartridge to displace the piston in a distal direction along a longitudinal axis of the housing,
a last dose sleeve rotatably supported in the housing and being selectively engageable with a user operable dose setting member for setting the dose, wherein the last dose sleeve is configured to be coupled to the dose setting member during dose setting and to be decoupled from the dose setting member during dose dispensing, wherein the last dose sleeve is axially fixed relative to the housing, and
a last dose member threadedly engaged and rotatable relative to the housing, rotationally locked to the last dose sleeve, and axially displaceable relative to the last dose sleeve, wherein the last dose member comprises a radial counter stop configured to engage with the radial stop to prevent rotation of the last dose member;
wherein the last dose sleeve is hollow, and at least one axially extending clutch member extending through the last dose sleeve is axially displaceable relative to the last dose sleeve for selectively engaging the dose setting member with the last dose sleeve exclusively during the dose setting.

17. The drug delivery device according to claim 16, wherein:
the last dose member is radially sandwiched between the housing and the last dose sleeve, and
the last dose sleeve is axially constrained in the housing between a drive wheel and an insert axially fixed to the housing.

18. The drug delivery device according to claim 16, wherein the last dose member is configured to jointly rotate with the last dose sleeve and to move axially relative to the last dose sleeve during the dose setting.

19. The drug delivery device according to claim 16, wherein the last dose member and the last dose sleeve are configured to be axially fixed relative to the housing during the dose dispensing.

20. The drug delivery device according to claim 16, wherein the radial stop and the radial counter stop extend in both a radial direction and an axial direction, and the radial stop is configured to engage with the radial counter stop in a circumferential direction such that further rotation of the last dose sleeve and further rotation of the last dose member are prevented when a last dose stop configuration of the drive mechanism has been reached.

21. A method of operating a drug delivery device, the method comprising:

setting a dose of medicament to be dispensed by the drug delivery device by operating a dose setting member, thereby causing a last dose sleeve axially fixed relative to a housing of the drug delivery device to rotate through the housing of the drug delivery device while a last dose member threadedly engaged to the housing of the drug delivery device, rotatable relative to the housing of the drug delivery device, and rotatably locked to the last dose sleeve advances axially through the housing of the drug delivery device, the last dose member being configured to inhibit rotation of the last dose sleeve to inhibit the dose from exceeding an amount of medicament remaining in the drug delivery device, a radial counter stop of the last dose member being configured to abut a radial stop on the housing of the drug delivery device, thereby inhibiting rotation of the last dose sleeve relative to the housing of the drug delivery device, wherein the last dose sleeve is hollow, and at least one axially extending clutch member extending through the last dose sleeve is axially displaceable relative to the last dose sleeve for selectively engaging the dose setting member with the last dose sleeve exclusively during dose setting; and dispensing the dose without causing the last dose member to advance axially through the housing while the last dose member is decoupled from the dose setting member.

22. The method according to claim 21, wherein setting the dose comprises rotating the dose setting member, wherein the last dose member is configured to inhibit rotation of the dose setting member to inhibit the dose from exceeding the amount of medicament remaining in the drug delivery device.

23. The method according to claim 22, wherein rotating the dose setting member causes rotation of a drive sleeve in a dose incrementing direction to set the dose, and dispensing the dose comprises depressing a dose dispensing button to disengage the dose setting member from the drive sleeve and to enable rotation of the drive sleeve in a dose decrementing direction to dispense the dose.

24. The method according to claim 21, wherein the radial stop and the radial counter stop extend in both a radial direction and an axial direction, and the radial stop is configured to engage with the radial counter stop in a circumferential direction such that further rotation of the last dose sleeve and rotation of the last dose member are prevented when a last dose stop configuration of the drug delivery device has been reached.

* * * * *

UNITED STATES PATENT AND TRADEMARK OFFICE
CERTIFICATE OF CORRECTION

PATENT NO. : 10,307,541 B2  
APPLICATION NO. : 14/783514  
DATED : June 4, 2019  
INVENTOR(S) : Stefan Bayer et al.

Page 1 of 1

It is certified that error appears in the above-identified patent and that said Letters Patent is hereby corrected as shown below:

In the Claims

In Column 24, Line 50, Claim 17, delete "member;" and insert -- member, --

Signed and Sealed this
Twenty-seventh Day of August, 2019

Andrei Iancu
*Director of the United States Patent and Trademark Office*